United States Patent
Qin et al.

[11] Patent Number: 6,036,676
[45] Date of Patent: Mar. 14, 2000

[54] SURFACE MODIFIED POLYMERIC MATERIAL FORMULATION

[75] Inventors: Chuan Qin, Gurnee; Patrick T. Ryan, Crystal Lake; Donna L. Rostron, Bartlett; Birendra K. Lal, Lake Zurich; Yuanpang S. Ding, Vernon Hills; Susan R. Mizener, Round Lake Heights; Lecon Woo, Libertyville; Michael T. K. Ling, Vernon Hills, all of Ill.; John O'Connor, Wallingford, Conn.

[73] Assignee: Baxter International Inc., Deerfield, Ill.

[21] Appl. No.: 09/018,668

[22] Filed: Feb. 4, 1998

Related U.S. Application Data

[63] Continuation of application No. 08/642,276, May 3, 1996, abandoned.

[51] Int. Cl.⁷ .................................................. A61M 5/00
[52] U.S. Cl. .......................................... 604/264; 604/265
[58] Field of Search ...................................... 604/264, 265

[56] References Cited

U.S. PATENT DOCUMENTS

| | | |
|---|---|---|
| 813,918 | 2/1906 | Schmitz . |
| 2,551,710 | 5/1951 | Slaughter . |
| 3,157,724 | 11/1964 | Salyer et al. . |
| 3,218,380 | 11/1965 | Euling et al. . |
| 3,260,776 | 7/1966 | Lindstrom, Jr. et al. . |
| 3,536,693 | 10/1970 | Schroeder et al. .................. 526/352.2 |
| 3,546,161 | 12/1970 | Wolheim .............................. 524/249 |
| 3,581,776 | 6/1971 | Sheahan . |
| 3,720,652 | 3/1973 | Yagi et al. ............................ 524/249 |
| 3,775,523 | 11/1973 | Haley . |
| 3,829,408 | 8/1974 | Wolkowicz .......................... 524/249 |
| 3,856,889 | 12/1974 | McConnell . |
| 3,886,227 | 5/1975 | VanBrederode et al. . |
| 3,974,240 | 8/1976 | Bock et al. . |
| 4,014,369 | 3/1977 | Kobres, Jr. . |
| 4,157,194 | 6/1979 | Takahashi . |
| 4,157,235 | 6/1979 | Lagabe et al. . |
| 4,193,899 | 3/1980 | Brenner et al. . |
| 4,212,966 | 7/1980 | McClain et al. ..................... 526/352.2 |
| 4,314,040 | 2/1982 | Castro et al. ........................ 524/249 |
| 4,337,188 | 6/1982 | Climenhage et al. ................ 524/249 |
| 4,374,882 | 2/1983 | Harlan . |
| 4,412,025 | 10/1983 | Corwin et al. ....................... 524/243 |
| 4,422,999 | 12/1983 | Mitchell . |
| 4,444,817 | 4/1984 | Subramanian . |
| 4,613,533 | 9/1986 | Loomis et al. . |
| 4,623,567 | 11/1986 | Hert . |
| 4,678,834 | 7/1987 | Boivin et al. . |
| 4,698,196 | 10/1987 | Fabian . |
| 4,721,637 | 1/1988 | Suzuki et al. . |
| 4,737,547 | 4/1988 | White . |
| 4,803,259 | 2/1989 | Zboril et al. ........................ 524/249 |
| 4,829,114 | 5/1989 | Trotoir et al. ....................... 524/243 |
| 4,886,634 | 12/1989 | Strutzel et al. . |
| 4,906,496 | 3/1990 | Hosono et al. . |
| 4,948,643 | 8/1990 | Mueller . |
| 4,957,974 | 9/1990 | Ilenda et al. . |
| 5,018,945 | 5/1991 | D'Silva . |
| 5,045,620 | 9/1991 | Itaba et al. . |
| 5,048,572 | 9/1991 | Levine . |
| 5,151,019 | 9/1992 | Danby et al. . |
| 5,169,708 | 12/1992 | Amaral et al. . |
| 5,225,451 | 7/1993 | Rogers et al. . |
| 5,234,731 | 8/1993 | Ferguson ............................ 526/352.2 |
| 5,241,031 | 8/1993 | Mehta . |

(List continued on next page.)

FOREIGN PATENT DOCUMENTS

| | | |
|---|---|---|
| 250874 | of 0000 | Czech Rep. . |
| 250874 | 8/1988 | Czech Rep. . |
| 0 133 355 A2 | 7/1983 | European Pat. Off. . |
| 211 651 | 2/1987 | European Pat. Off. . |
| 0 256 644 | 2/1988 | European Pat. Off. . |
| 0 450 088 A1 | 10/1991 | European Pat. Off. . |
| WO 92/18173 | 10/1992 | European Pat. Off. . |
| 0 573 884 A2 | 6/1993 | European Pat. Off. . |
| 07205275 | 8/1995 | European Pat. Off. . |
| 1928843 | 12/1990 | Germany . |
| 4332624 | 11/1992 | Japan . |
| 5-017639 | 1/1993 | Japan . |
| 7-205276 | 8/1995 | Japan . |
| WO 80/02671 | 12/1980 | WIPO . |
| WO 93/23093 | 11/1993 | WIPO . |
| WO 94/26793 | 11/1994 | WIPO . |
| WO 96/08520 | 3/1996 | WIPO . |
| WO 96/36374 | 11/1996 | WIPO . |
| PCT/US97/07032 | 8/1997 | WIPO . |
| PCT/US97/07033 | 8/1997 | WIPO . |

OTHER PUBLICATIONS

WO 90/06139 (Howard, G.E.) Jun. 24, 1994.

Functionalized Modified High Melt Flow Polyolefins, Wilpers et al., United States Statutory Invention Registration No. H1419.

The Effect of Plastic Formulation Variables on Bond Strengths Achieved With Typical Medical Device Adhesives, presented at Manufacturing Medical Plastics '95 by Pat Courtney, Senior Application Engineer, Loctite Corporation.

European Plastic News, Jun., 1996; *Medical Tubes Use Metallocene Resin* p. 17.

Patrick J. Courtney and James Serenson, "Adhesive Bonding of Medical Plastics: An Overview", Jan./Feb. 1996 Medical Plastics and Biomaterials, pp. 20–25.

*Primary Examiner*—Veronica P. Hoke
*Attorney, Agent, or Firm*—Mark J. Buonaiuto; Joseph A. Fuchs

[57] ABSTRACT

The present invention provides a polymeric blend suitable for adhesive bonding to polar polymeric materials comprising an ultra-low density polyethylene in an amount by weight within the range of 99.999%–90.0%; and an additive selected from the group consisting of polyoxyethylene(5) oleylamine, bis(2-hydroxyethyl)soyaamine, bis(2-hydroxyethyl)oleylamine, and polyoxyethylene(5) octadecylamine, the additive in an amount by weight within the range of 0.001%–10%.

5 Claims, 1 Drawing Sheet

U.S. PATENT DOCUMENTS

| | | |
|---|---|---|
| 5,264,488 | 11/1993 | Takeuchi et al. . |
| 5,274,035 | 12/1993 | Chundury . |
| 5,281,670 | 1/1994 | Lee et al. . |
| 5,343,738 | 9/1994 | Skaggs . |
| 5,346,732 | 9/1994 | Lai et al. ............................ 526/352.2 |
| 5,439,454 | 8/1995 | Lo et al. . |
| 5,525,388 | 6/1996 | Wand et al. . |
| 5,529,176 | 6/1996 | Namba et al. ........................ 524/249 |
| 5,562,127 | 10/1996 | Fanselow et al. . |
| 5,573,822 | 11/1996 | Nishikawa et al. . |
| 5,620,760 | 4/1997 | Galimberti et al. . |
| 5,629,059 | 5/1997 | Desai et al. . |
| 5,638,660 | 6/1997 | Kuo . |

SURFACE MODIFIED POLYMERIC MATERIAL FORMULATION

This is a continuation of U.S. patent application Ser. No. 08/642,276 filed May 3, 1996, now abandoned.

TECHNICAL FIELD

This invention relates to polyolefin blends to be fabricated into medical tubings and more specifically, to a surface modified polyolefin tubing especially suitable for adhesive bonding to rigid housings using cyanoacrylate adhesives.

RELATED APPLICATIONS

This application is a continuation of U.S. patent application Ser. No. 08/642,276 now abandoned. U.S. patent application Ser. No. 08/642,276 is hereby incorporated herein by reference, and made a part hereof.

BACKGROUND ART

In the medical field, where beneficial agents are collected, processed and stored in containers, transported and ultimately delivered through tubes by infusion to patients, there has been a recent trend toward developing materials useful for fabricating such containers and tubing without the disadvantages of currently used materials such as polyvinyl chloride. These new materials for tubings must have a unique combination of properties, so that the tubing may be used in fluid administration sets. Among these are the materials must be optically clear, environmentally compatible, have sufficient yield strength and flexibility, have a low quantity of low molecular weight additives, and be compatible with medical solutions.

It is desirable for medical tubing to be optically transparent to allow for visual inspection of fluids in the tubing.

It is also a requirement that the tubing materials be environmentally compatible as a great deal of medical tubing is disposed of in landfills and through incineration. Further benefits are realized by using a material which is thermoplastically recyclable so that scrap generated during manufacturing may be incorporated into virgin material and refabricated into other useful articles.

For tubing that is disposed of by incineration, it is necessary to use a material that does not generate or minimizes the formation of by-products such as inorganic acids which may be environmentally harmful, irritating, and corrosive. For example, PVC may generate objectionable amounts of hydrogen chloride (or hydrochloric acid when contacted with water) upon incineration, causing corrosion of the incinerator and possible pollution to the environment.

To be compatible with medical solutions, it is desirable that the tubing material be free from or have a minimal content of low molecular weight additives such as plasticizers, stabilizers and the like. These components could be extracted into the therapeutic solutions that come into contact with the material. The additives may react with the therapeutic agents or otherwise render the solution ineffective. This is especially troublesome in bio-tech drug formulations where the concentration of the drug is measured in parts per million (ppm), rather than in weight or volume percentages. Even minuscule losses of the bio-tech drug can render the formulation unusable. Because bio-tech formulations can cost several thousand dollars per dose, it is imperative that the dosage not be changed.

Polyvinyl chloride ("PVC") has been widely used to fabricate medical tubings as it meets most of these requirements. However, because PVC by itself is a rigid polymer, low molecular weight components known as plasticizers must be added to render PVC flexible. As set forth above, these plasticizers may leach out of the tubing and into the fluid passing through the tubing to contaminate the fluid or to render the fluid unusable. For this reason, and because of the difficulties encountered in incinerating PVC, there is a need to replace PVC medical tubing.

Polyolefins have been developed which meet many of the requirements of medical containers and tubing, without the disadvantages associated with PVC. Polyolefins typically are compatible with medical applications because they have minimal extractability to the fluids and contents which they contact. Most polyolefins are environmentally sound as they do not generate harmful degradants upon incineration, and in most cases are capable of being thermoplastically recycled. Many polyolefins are cost effective materials that may provide an economic alternative to PVC. However, there are many hurdles to overcome to replace all the favorable attributes of PVC with a polyolefin.

For example, because of the inert nature of polyolefins, due in part to the non-polar nature of the polymer, difficulties have been encountered in bonding the polyolefin materials to polar molecules, such as polycarbonates and acrylic polymers. Typically, medical containers such as I.V. bags are connected to a patient through a series of connected tubing that have drip chambers, Y-type injection sites, venous catheters and the like between the bag and the patient. Many of these components include rigid housings manufactured from polymers such as polycarbonates, acrylics and copolyesters. The housings have sleeves in which the tubing is inserted in a telescoping fashion to attach the tube to the housing. Therefore, it is necessary for the medical tubing to be connected to the rigid housing to form a fluid tight seal with the housings.

PVC tubing is typically secured within such housings using solvent bonding techniques. Solvent bonding requires exposing the end of the tubing to be inserted into the housing to a solvent such as cyclohexanone or methyl ethyl ketone. The solvent effectively softens or "melts" the PVC so when the tubing is inserted into the housing, a bond is formed. It is desirable that the outer tubing diameter be approximately the same dimension or slightly larger than the inner diameter of the housing to form an interference fit, as close tolerances in these dimensions assists in forming a secure bond.

Solvent bonding techniques, however, are ineffective on certain polyolefins including polyethylene. Problems have also been encountered in using adhesive bonding techniques.

One attempt at overcoming this problem was to use a two step process of applying a primer material to the surface to be bonded followed by an adhesive. Cyanoacrylate adhesives have worked with some success using this technique with a primer. However, the two step process adds an additional step to a manufacturing process which could slow down the production line and increase the labor costs. Further, primers increase the cost of the process. Third, because primers typically contain large quantities of volatile chemicals such as organic solvents, and might lead to toxicity, safety and environmental problems. Fourth, primers may limit manufacturing options as they have a limited on-part life time, i.e., the primers will lose their activities within hours after exposure to an ambient environment.

The present invention solves these and other problems.

DISCLOSURE OF INVENTION

The present invention provides a polymeric blend for fabricating tubing. Such tubing is suitable for adhesive bonding to polar or non-polar polymeric materials with a cyanoacrylate adhesive. The blend comprises a polyethylene copolymer in an amount by weight within the range of about 90%–99.999% and an additive in an amount within the range of 10%–0.001%. The additive may be selected from the group consisting of polyoxyethylene(5)oleylamine, bis (2-hydroxyethyl)soyaamine, bis(2-hydroxyethyl) oleylamine, and polyoxyethylene(5)octadecylamine.

Tubing constructed from these blends show improved tensile strength when bonded to a polar housing as compared to tubing constructed without the additive. Further, the tubing constructed from the blend has improved on-part life of the additive when compared to tubing where a primer is sprayed on the surface of the polyethylene copolymer instead of an additive being incorporated into the blend. The on-part life means the period of time the additive is capable of adapting the polyethylene to bind to rigid housings using cyanoacrylate adhesives. Preferably the on-part life is greater than 72 hours and more preferably is greater than 6 weeks. By increasing the on-part life of the additive, the manufacturing options for forming tubing and housing assemblies has greatly expanded.

BEST MODE FOR CARRYING OUT THE INVENTION

Figure 1:
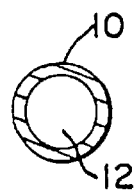
FIG. 1 is an enlarged cross-sectional view of a medical tubing fabricated from a polymer blend of the present invention.

While the invention is susceptible of embodiment in many different forms, there is shown in the drawings and will herein be described in detail preferred embodiments of the invention with the understanding that the present disclosure is to be considered as an exemplification of the principles of the invention and is not intended to limit the broad aspect of the invention to the embodiments illustrated.

I. Polymer Blends

The polymer blends of the present invention include polyethylene copolymers and an additive. The polyethylene copolymers are selected from the group of ethylene copolymerized with comonomers selected from alpha-olefins such as butene-1 or octene-1. These copolymers shall be referred to as ultra-low density polyethylenes, i.e., those having a density of less than about 0.910 g/cm$^3$. The preferred additive may be selected from the group consisting of polyoxyethylene(5)oleylamine (Ethomeen 0/15, Akzo Nobel Chemical Company), bis(2-hydroxyethyl)soyaamine (Ethomeen S/12), bis(2-hydroxyethyl)oleylamine (Ethomeen 0/12), and polyoxyethylene(5)octadecylamine (Ethomeen 18/15). The polymer blends are capable of being fabricated into medical tubing and attached to rigid polymers using cyanoacrylate adhesives.

The blends should have the polyethylene copolymer in an amount by weight within the range of 90%–99.999%, more preferably 98.0%–99.99%. The additive should be in an amount by weight within the range of 0.001%–10%, and more preferably 0.01%–2%.

The components of the polymer blends should be blended through molten mixing, physical blending or the like.

II. Method of Fabricating Medical Tubing

FIG. 1 shows medical tubing 10 of the present invention fabricated from one of the blends of the present invention and having a fluid passageway 12. The medical tubing 10 is preferably fabricated by an extrusion process.

III. Rigid Medical Housings

Figure 2:
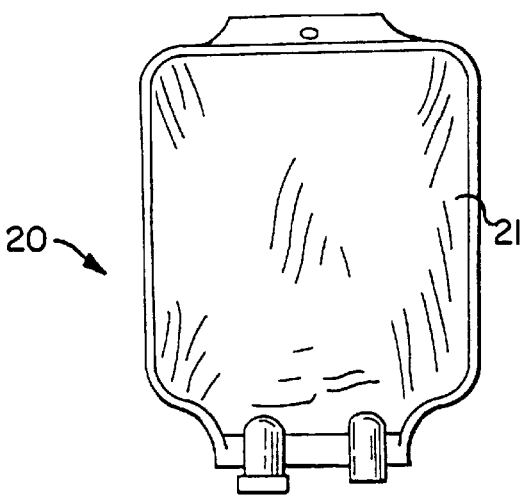
FIG. 2 is a schematic view of gravity pressurized fluid administration set.
Figure 2:
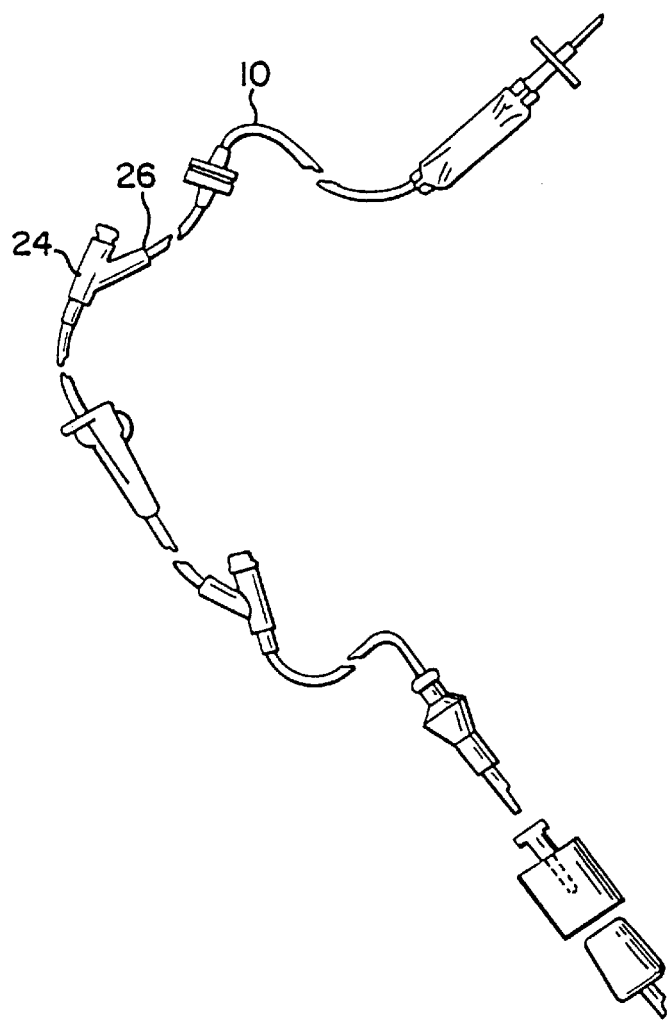

The administration set 20 in FIG. 2 includes tubing 10 connected to a fluid or I.V. container 21 which is in fluid communication with various rigid plastic housings such as Y-type injection sites 24 through tubing 10. The tubing 10 connects to a housing sleeve 26 on the housing 22.

The housing 24 and its housing sleeve 26 is preferably constructed of a rigid polymer such as polycarbonates, copolyesters, acrylics, ABS, nylon, polystyrene, polypropylene, polyethylene, polysulfone, and polyimide. The term "Rigid polymers" are those having a modulus of elasticity of greater than 50,000 psi and preferably greater than 100,000 psi. Typically, the housings are constructed using injection molding techniques.

Suitable adhesives for attaching the tubing 10 to the housing 24 include the family of cyanoacrylate adhesives.

IV. Examples

An ultra-low density polyethylene sold under the product designation Exact 4011 (Exxon Chemical Company) was tumble blended with polyoxyethylene(5)oleylamine which is sold under the product designation Ethomeen 0/15 (Akzo Nobel Chemical Company). The blend had 0.23 weight percent of the Ethomeen and the remainder the Exact 4011.

The blend was extruded into tubing having an outer diameter within the range of 0.139–0.145 inches and an inner diameter within the range of 0.101–0.105 inches. The tubing was cut into three inch segments for testing. A cyanoacrylate adhesive sold by Loctite under the product number 4061 was used to connect the tubing segments to an acrylic luer housing.

The luer housing has an opening having a diameter of 0.150 inches that leads to a chamber having diametrically inwardly tapering sidewalls to a dimension of 0.142 inches. An end of the tubing is inserted into the opening of the luer to form an interference fit in the luer chamber. A quantity of the cyanoacrylate is added to the luer opening which wicks about the outer circumference of the tubing.

The tensile strength of the tubing and housing assemblies were tested using an Ametek apparatus. The tubing and housing assemblies were mounted on an Ametek where a pull test study was conducted. The force required to break either the tubing or the bond was found to be on average 6.826 pounds.

This tensile strength compares favorably with the tensile strength of tubing constructed from ultra-low density polyethylene sold under the product designation Exact 4011 (Exxon Chemical Company) without any additive. The tensile strength of the tubing joint without the additive was measured in accordance with the above procedure. The force required to break either the tubing or the bond was found to be on average 3.66 pounds.

As stated above, by incorporating the additive Ethomeen 0/15 (Akzo Nobel Chemical Company) into the blend, the on-part life of the additive was increased. Tubing made in accordance with the present invention has been found to be effective in forming secure adhesive bonds with rigid housings even after 6 weeks. For tubing where the primer is sprayed onto the outer surface of the polyethylene copolymer, the on-part life is roughly 24 hours.

While specific embodiments have been illustrated and described, numerous modifications are possible without departing from the spirit of the invention, and the scope of protection is only limited by the scope of the accompanying claims.

We claim:

1. A medical tubing having a modified surface for improved cyanoacrylate adhesive bonding to rigid, polar polymers comprising:

an ethylene copolymerized with a comonomer selected from α-olefins and having a density less than about 0.910 g/cm$^3$; and an additive selected from the group consisting of polyoxyethylene(5)oleylamine, bis(2-hydroxyethyl) soyaamine, bis(2-hydroxyethyl)oleylamine, and polyoxyethylene(5)octadecylamine.

2. The tubing of claim 1 wherein the amount by weight of the ethylene and α-olefin copolymer is within the range of 99.999%–90.0%, and the amount by weight of the additive is within the range of 0.001%–10%.

3. The tubing of claim 1 wherein the tubing has an on-part life of the additive of greater than 72 hours.

4. A medical assembly for connecting a medical container to a patient, the assembly comprising:

a tubing formed from an ethylene copolymerized with a comonomer selected from α-olefins and having a density less than about 0.910 g/cm$^3$, and an additive selected from the group consisting of polyoxyethylene (5)oleylamine, bis(2-hydroxyethyl)soyaamine, bis(2-hydroxyethyl)oleylamine, and polyoxyethylene(5) octadecylamine;

a polar polymer housing having a sleeve; and a first end of the tubing inserted into the sleeve and a cyanoacrylate adhesive connecting the first end of the tubing to the housing.

5. The medical assembly of claim 4, wherein the polar polymer housing comprises a polymer selected from the group consisting of polycarbonates, copolyesters, acrylics, nylon, polystyrene, polysulfone, and polyamide.

* * * * *